United States Patent
Knox

(10) Patent No.: US 12,257,453 B2
(45) Date of Patent: Mar. 25, 2025

(54) CONTROL OF A RADIOTHERAPY DEVICE

(71) Applicant: Elekta Limited, Crawley (GB)

(72) Inventor: Chris Knox, Crawley (GB)

(73) Assignee: Elekta Limited, Crawley (GB)

( * ) Notice: Subject to any disclaimer, the term of this patent is extended or adjusted under 35 U.S.C. 154(b) by 34 days.

(21) Appl. No.: 18/040,476

(22) PCT Filed: Aug. 19, 2021

(86) PCT No.: PCT/EP2021/073059
§ 371 (c)(1),
(2) Date: Feb. 3, 2023

(87) PCT Pub. No.: WO2022/038232
PCT Pub. Date: Feb. 24, 2022

(65) Prior Publication Data
US 2024/0252838 A1   Aug. 1, 2024

(30) Foreign Application Priority Data
Aug. 19, 2020 (GB) ..................................... 2012946

(51) Int. Cl.
*A61N 5/10* (2006.01)

(52) U.S. Cl.
CPC .......... *A61N 5/103* (2013.01); *A61N 5/1045* (2013.01); *A61N 5/1067* (2013.01); *A61N 5/107* (2013.01);
(Continued)

(58) Field of Classification Search
None
See application file for complete search history.

(56) References Cited

U.S. PATENT DOCUMENTS

| 6,245,005 B1* | 6/2001 | von Gutfeld | A61N 5/1048 600/1 |
| 2005/0152495 A1* | 7/2005 | Hesse | A61N 5/1049 378/65 |

(Continued)

FOREIGN PATENT DOCUMENTS

WO    WO-2011073820 A1    6/2011

OTHER PUBLICATIONS

"International Application Serial No. PCT/EP2021/073059, International Search Report dated Dec. 23, 2021", (Dec. 23, 2021), 5 pgs.
(Continued)

*Primary Examiner* — Marcus H Taningco
(74) *Attorney, Agent, or Firm* — Schwegman Lundberg & Woessner, P.A.

(57) ABSTRACT

A radiotherapy device, a computer-implemented method and a computer-readable medium are disclosed. The radiotherapy device includes a radiation source, one or more imaging systems and a controller communicatively coupled to the radiation source and the one or more imaging systems. The radiation source is configured to apply radiation to a treatment region coinciding with a subject according to a treatment plan. The one or more imaging systems are configured to generate image data for the subject. The controller is configured to: determine, based on the image data, a relative distance between a target region of the subject and an organ at risk of the subject, wherein the treatment plan comprises a prescribed dose for the target region; determine a buffer region around the target based at least in part on the relative distance; and generate a control signal for adjusting a radiotherapy treatment in response to determining, based on the image data, that the treatment region is located at least partially outside the buffer region.

23 Claims, 6 Drawing Sheets

(52) U.S. Cl.
CPC .... *A61N 5/1081* (2013.01); *A61N 2005/1074* (2013.01)

(56) References Cited

U.S. PATENT DOCUMENTS

| | | | |
|---|---|---|---|
| 2008/0269607 A1* | 10/2008 | Ishida | A61N 7/02 600/439 |
| 2010/0189319 A1* | 7/2010 | Wu | G06V 10/755 382/128 |
| 2011/0137158 A1 | 6/2011 | Sumanaweera et al. | |
| 2012/0280135 A1* | 11/2012 | Bal | A61N 5/1039 250/336.1 |
| 2013/0077752 A1 | 3/2013 | Zankowski et al. | |
| 2017/0050051 A1 | 2/2017 | Berbeci et al. | |
| 2018/0078792 A1 | 3/2018 | Ollila et al. | |
| 2018/0099151 A1* | 4/2018 | Sullivan | A61N 5/1031 |
| 2018/0318604 A1 | 11/2018 | Schadewaldt et al. | |
| 2018/0326223 A1 | 11/2018 | Willcut | |
| 2020/0323510 A1* | 10/2020 | Maltz | A61N 5/1039 |
| 2023/0149741 A1* | 5/2023 | Hirai | G06T 7/33 378/4 |

OTHER PUBLICATIONS

"International Application Serial No. PCT/EP2021/073059, Written Opinion dated Dec. 23, 2021", (Dec. 23, 2021), 7 pgs.

"United Kingdom Application Serial No. 2012946.6, Examination Report dated Jan. 29, 2021", (Jan. 29, 2021), 6 pgs.

"Chapter 6 of Mridian Linac System Version5 L-0086", ViewRay, Inc.

Van Herk, Marcel, "The probability of correct target dosage: dose-population histograms for deriving treatment margins in radiotherapy", International Journal of Radiation Oncology* Biology* Physics 47.4, (2000), pp. 1121-1135.

* cited by examiner

CONTROL OF A RADIOTHERAPY DEVICE

PRIORITY APPLICATIONS

This application is a U.S. National Stage Filing under 35 U.S.C. § 371 from International Application No. PCT/EP2021/073059, filed on Aug. 19, 2021, and published as WO2022/038232 on Feb. 24, 2022, which claims the benefit of priority to British Application No. 2012946.6, filed on Aug. 19, 2020; the benefit of priority of each of which is hereby claimed herein, and which applications and publication are hereby incorporated herein by reference in their entireties.

This disclosure relates to generating control signals configured to control operation of a radiotherapy device, and in particular to generating control signals configured to control operation of a radiotherapy device based on locations of organs at risk.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In radiotherapy treatment, it is desirable to deliver a prescribed dose of radiation to a target region of a subject and to limit irradiation of other parts of the subject, i.e. to healthy tissue. Motion of the subject can cause a decreased dose to be applied to the target region and/or an increased dose to be applied to the healthy tissue. There are various physiological motions that can contribute to a total motion of a subject. Gross or large-scale movements of a subject may include shifting position, coughing or sneezing. The subject may also undergo cyclical, physiological movement. For example, the subject may undergo respiratory motion due to their breathing cycle and may undergo cardiac motion based on beating of their heart. To address this motion, known techniques include monitoring a location and/or movement of the subject and gating the treatment beam such that radiation is applied only when the subject (i.e. the target region within the subject) is in a desired location and not when the subject/target region is in a suboptimal location. In other words, radiation may be applied or not applied (i.e. the beam is gated) based on sensed movements or locations of the subject. Other known techniques for addressing movement of the subject include training a patient's breathing or asking the patient to hold their breath during radiotherapy treatment.

In prior approaches using X-ray imaging modalities, it is typically only possible to see bony anatomy of a subject. Using these approaches, it may not be possible to determine locations of a target region or of organs within the subject during a treatment. Therefore, the application or gating of radiotherapy may not be as accurate as desired. Some prior approaches have used magnetic resonance (MR) imaging integrally with application of radiotherapy to determine whether a target region is in a desired location. One such approach can be performed using the Clarity VOICE software. MR imaging information can be used to inform the gating so as to provide more accurate gating. The radiation may only be applied when a target region is in a specific location, or within a certain tolerance of this specific location, as determined using the MR imaging.

Currently, gating of a radiotherapy beam is driven based on a constant margin around the target. The constant margin may be of a constant predefined width around the target or may have a constant width around the target set to a maximum absolute distance a centre of mass of the target can move without coinciding with particular structures. During a radiotherapy treatment, a subject may move such that the target moves by a corresponding or similar distance. If, as a result of this, radiation is applied to locations outside the constant margin around the target, i.e. if it is determined that there is an overlap between an area where the radiation is applied and an area where radiation should not be applied, the beam can be gated such that radiation is no longer applied. This helps to ensure adequate irradiation of the target and to prevent substantial irradiation of healthy tissue. The constant margin defined may typically be of a uniform, relatively narrow width as part of a conservative, cautious or risk-averse approach. This may especially be the case if there is significant uncertainty in the positions or movements of the subject or parts of the subject based on the techniques used to monitor the subject.

However, there are various possible locations of the target (tumour) within the body of the subject, and the anatomy surrounding the target will vary greatly dependent on its location within the body. Moreover, the surroundings of a target are generally different in different (three-dimensional) directions. While it is desirable to avoid irradiation of any healthy tissue, the risks associated with irradiating certain healthy tissue, for example organs at risk, may be more severe compared with the risks associated with other healthy tissue. By not taking into account such variations in risk, prior approaches may apply an inappropriately cautious approach to application of radiotherapy which may lead to suboptimal radiotherapy treatment. Setting an inappropriately wide margin may lead to unsafe irradiation of an organ at risk, while setting an inappropriately narrow margin may lead to unnecessary gating of the treatment beam. Some healthy tissue can withstand low or moderate doses of radiation such that gating of the radiotherapy beam in some scenarios may lead to unnecessarily delayed or inefficient radiotherapy treatment.

It would be advantageous to provide improved means of accounting for and reacting to patient motion during radiotherapy treatment. Moreover, it would be advantageous to provide improved consideration of the anatomical surroundings of a target when controlling a treatment beam. Therefore, it would be advantageous to provide more accurate control of a treatment beam. In addition, it would be advantageous to provide more efficient radiotherapy treatment and higher patient throughout.

The present invention seeks to address these and other disadvantages encountered in the prior art.

SUMMARY

An invention is set out in the independent claims.

According to an aspect, there is provided a radiotherapy device comprising: a radiation source configured to apply radiation to a treatment region coinciding with a subject according to a treatment plan; one or more imaging systems configured to generate image data for the subject; and a controller communicatively coupled to the radiation source and the one or more imaging systems, the controller being configured to: determine, based on the image data, a relative distance between a target region of the subject and an organ at risk of the subject, wherein the treatment plan comprises a prescribed dose for the target region; determine a buffer region around the target region based at least in part on the relative distance; and generate a control signal for adjusting a radiotherapy treatment in response to determining, based on the image data, that the treatment region is located at least partially outside the buffer region.

According to another aspect, there is provided a computer-implemented method comprising: receiving image data for a subject from one or more imaging systems; determining, based on the image data, a relative distance between a target region of the subject and an organ at risk of the subject, wherein a treatment plan comprises a prescribed dose for the target region; determining a buffer region around the target region based at least in part on the relative distance; and generating a control signal for adjusting a radiotherapy treatment in response to a treatment region coinciding with the subject being located at least partially outside the buffer region.

According to another aspect, there is provided a computer-readable medium comprising computer executable instructions which, when executed by a processor, cause the processor to perform the method described above.

FIGURES

Specific embodiments are now described, by way of example only, with reference to the drawings, in which.

DETAILED DESCRIPTION

The present disclosure relates to improved control of the operation of a radiotherapy device. A radiotherapy device can include a radiation source configured to apply radiation to a treatment region of a subject and one or more imaging systems configured to generate image data for the subject. A controller communicatively coupled to the radiation source and the one or more imaging systems can be configured to determine, based on the image data, a relative distance between a target region (i.e. including a tumour) and an organ at risk (i.e. healthy tissue comprising a critical structure sensitive to irradiation). The controller can further be configured to determine a buffer region around the target region based at least in part on the relative distance. The buffer region can be of different widths in different directions. In particular, the buffer region can have a smaller width in a direction of the organ at risk and a larger width in a different direction that does not correspond to a location of an organ at risk. The controller can further be configured to determine that the treatment region is located at least partially outside the buffer region. This determination can be based on the image data generated by the one or more imaging systems. The controller can be configured to generate a control signal for adjusting a radiotherapy treatment in response to determining that the treatment region is located at least partially outside the buffer region. The control signal can be configured to adjust an output of the radiation source. For example, the control signal can be configured to gate the radiation source. In this manner, a gating algorithm can be driven based on a flexible, anisotropic buffer region surrounding a target region and based on an anatomy of a subject. The control signal can be configured to adjust, i.e. to reduce, a dose rate applied by the radiation source. In this manner, the dose rate can be reduced to a level acceptable for an organ at risk using the flexible, anisotropic buffer region and according to the anatomy of the subject. The control signal can be configured to adjust a location and/or orientation of the radiotherapy source, to adjust a shape of a radiotherapy beam, and/or to adjust a location and/or orientation of a patient positioning surface. This can enable the treatment region to be dynamically realigned with the target region and can prevent regions outside the target region from being irradiated. These techniques can accommodate and mitigate the higher risks associated with irradiating an organ at risk while avoiding unnecessary halting of a radiotherapy treatment.

Figure 1:
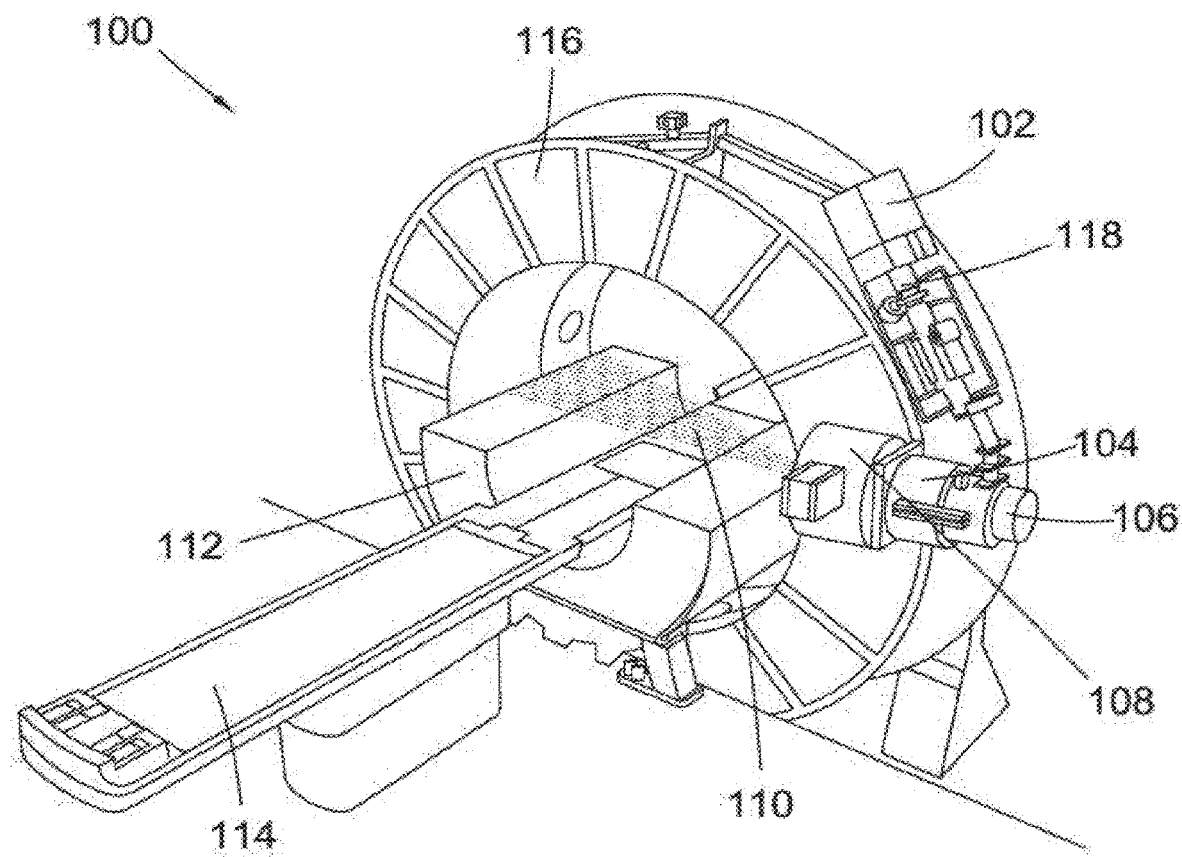
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the subject support surface. The controller is communicatively coupled to a memory, e.g. a computer readable medium.

The linac device also comprises several other components and systems as will be understood by the skilled person. For example, in order to ensure the linac does not leak radiation, appropriate shielding is also provided.

A treatment delivery may comprise application of radiation by the radiation source, for example according to a treatment plan. The radiation source may be rotated around the subject. Such rotation may be continuous or pseudo-continuous such that a dose is applied from a continuous or pseudo-continuous range of angles. In other examples, the rotation may be to a plurality of discrete angles such that a dose is applied from a discrete series of angles. The rotation of the radiation source may be predetermined according to the treatment plan. The treatment plan may comprise a prescribed dose (e.g. a clinically-prescribed dose) for the target region. The prescribed dose may be a function of spatial coordinates, for example in one, two or three spatial dimensions. For example, the prescribed dose may vary spatially to account for concentrations of unhealthy tissue within the subject.

Different subjects may have different distributions or concentrations of unhealthy tissue. For example, different subjects may have tumours of different sizes, different locations and/or different shapes. For this reason, a specific treatment plan may be determined for radiotherapy treatment of each subject and/or each tumour. Determining the treatment plan may involve acquiring data for the subject. For example, MR imaging, computerised tomography (CT), ultrasound and/or other techniques may be used to derive images of structures inside a subject's body. Alternatively, or in addition, data may be provided based on clinical (e.g. internal) examinations. This can provide information on the distribution of a tumour, as well as information on the distribution of healthy tissue, e.g. organs at risk (OARs).

Figure 2:
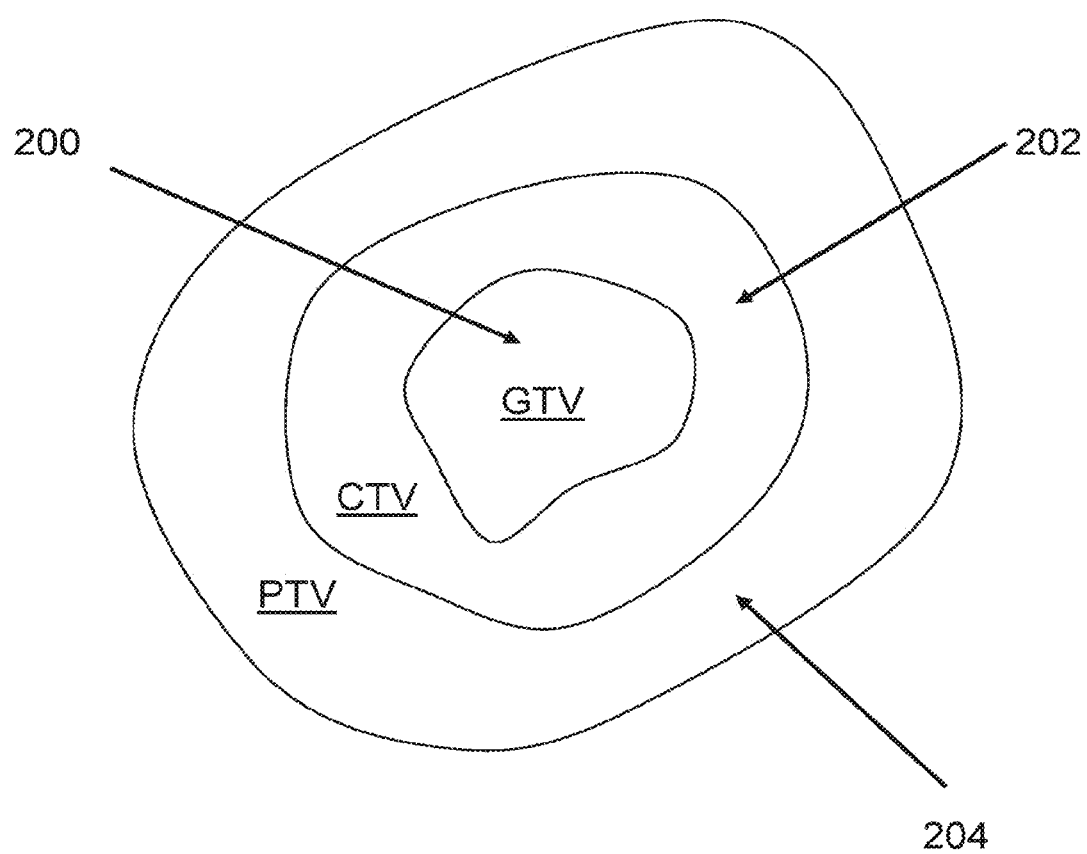
FIG. 2 depicts a schematic representation of defined regions according to the present disclosure.

In determining a treatment plan, one or more regions or volumes within the subject may be defined. FIG. 2 depicts a schematic representation of some of such regions or volumes according to the present disclosure. It will be appreciated that further and/or alternative volumes may be defined. A gross tumour volume (GTV) 200 may be defined as a gross, palpable, visible or clinically demonstrable location and extent of a malignant growth. A clinical target volume (CTV) 202 may be defined as a tissue volume that contains the GTV 200 as well as sub-clinical malignant disease which may be at risk and require treatment. The GTV 200 and the CTV 202 are therefore anatomical volumes within a subject that relate to a distribution of unhealthy tissue and/or to a probability of a distribution of unhealthy tissue. A planning target volume (PTV) 204 may be defined as a volume including the CTV 202 (and the GTV 200), as well as an additional margin to compensate for uncertainties and/or variations relating to the precision or setup of a radiotherapy beam and/or relating to positional uncertainty of the target region. The PTV 204 is therefore a geometrical volume used to select beam arrangements in order to apply a prescribed dose to the CTV 202. In determining the above-mentioned volumes and the treatment plan, simulation of an instance of radiotherapy treatment may be used to provide treatment beam geometries appropriate for particular target regions of the subject.

The GTV 200, CTV 202 and PTV 204 as depicted in FIG. 2 may correspond to the relative extent of these respective volumes in a certain plane, for example at a certain depth within a patient and at a certain orientation. At other depths and/or other orientations, the representations of the extents of these respective volumes may differ from those depicted in FIG. 2. The GTV 200, CTV 202 and PTV 204 as depicted in FIG. 2 provide a certain example of a distribution of unhealthy tissue, such as a tumour. It will be appreciated that various other subject-specific distributions may also occur and any such other distributions are considered to be within the present disclosure.

In some examples, the CTV 202 may extend beyond the GTV 200 by a different distance in different directions. In some examples, the extent of the CTV 202 may coincide with an extent of the GTV 200 at one or more points or in one or more directions. In some examples, the extent of the CTV 202 may differ from the extent of the GTV 200 by a constant distance. In some examples, the PTV 204 may extend beyond the GTV and/or the CTV 202 by a different distance in different directions. In some examples, the extent of the PTV 204 may coincide with an extent of the GTV 200 and/or the CTV 202 at one or more points or in one or more directions. In some examples, the extent of the PTV 204 may differ from the extent of the GTV 200 and/or the CTV 202 by a constant distance.

Based on the above considerations, and as part of the determination of the treatment plan, it may be determined that a certain prescribed dose of radiation should be applied to a certain target region or target volume of the subject. The terms target volume, target region and PTV 204 may be used interchangeably herein. The target region may be a two-dimensional region (i.e. an area) or a three-dimensional region (i.e. a volume). A constraint may be imposed that the PTV 204 should receive a prescribed dose of radiation as part of a radiotherapy treatment.

Based on the above considerations, determining a treatment plan may include using dose management/calculation software to indicate distributions of expected doses. For example, a voxel (i.e. a discrete volume element of a subject) may be associated with an expected dose. An isodose may be defined as an expected dose of equal intensity applied to more than one point. Therefore, an isodose curve may be defined as a line joining points receiving an equal expected dose. Similarly, an isodose surface may be defined as a surface joining points receiving an equal expected dose. In other words, all points on the isodose surface are expected to receive the same dose. As used herein, an isodose surface may be a two-dimensional surface enclosing an area or a three-dimensional surface enclosing a volume. While the Figures of the present disclosure depict two-dimensional views for ease of understanding, these may be understood as two-dimensional representations of three-dimensional features, for example projected onto two-dimensional planes.

Due to considerations relating to beam geometries, an expected dose may increase monotonically towards a central point with a maximum expected dose. The isodose surface may enclose a region within which a particular dose (or at least a particular dose) will be received. A treatment plan may be determined with a 'top hat' dose profile such that the expected dose distribution is flatter in a target region than at the immediate exterior of the target region, so as to provide a relatively constant expected dose at the target region and a relatively sharp drop-off in expected dose outside of the target region.

Figure 3A:
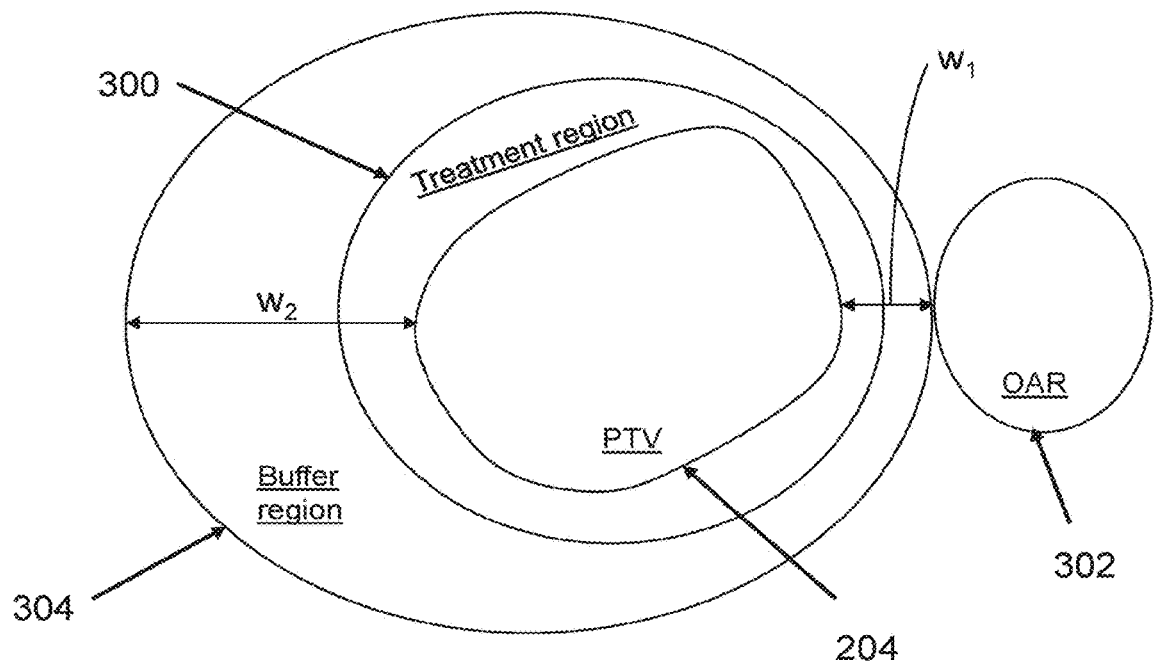
FIGS. 3a and 3b depict schematic representations of defined regions according to the present disclosure.
Figure 3B:
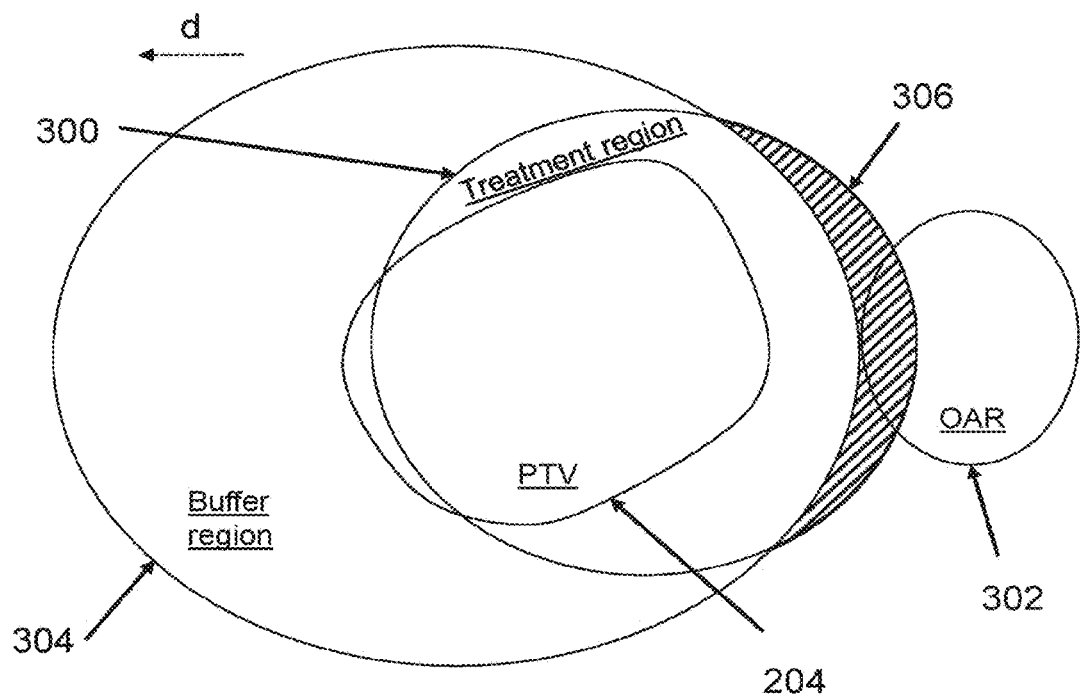

FIGS. 3a and 3b depict schematic representations of defined regions according to the present disclosure. FIG. 3a depicts a PTV 204, which may correspond to the PTV 204 of FIG. 2. In FIG. 3a, a GTV 200 and a CTV 202 have not been depicted for ease of understanding, though it will be understood that these may be considered to be nested within the PTV 204 in a similar manner to that shown in FIG. 2.

FIG. 3a also depicts a treatment region 300. The treatment region 300 includes the PTV 204. Due to limitations associated with irradiation techniques, it may not be possible or practical to irradiate a region corresponding exactly to the PTV 204 with a prescribed dose. For example, for some tumours, the PTV 204 may be of a particularly irregular shape, making it difficult to design and implement beam geometries and doses which irradiate the PTV 204 and only the PTV 204 with a prescribed dose. Therefore, the treatment region 300 may be larger than the PTV 204 and may be of a simpler shape than the PTV 204. It may be determined that the PTV 204 should receive at least a certain prescribed dose of radiation according to clinical requirements. The treatment region 300 is the region which is actually planned to receive at least this prescribed dose of radiation based on a treatment plan. The treatment region 300 may be described as a treatment region 300 of the subject, or as a treatment region 300 coinciding with the subject or a part of the subject.

FIG. 3a also depicts an organ at risk or OAR 302. Analogous to the extension of the CTV 202 to the PTV 204 to account for uncertainties, the OAR 302 may be extended to a Planning Risk Volume (PRV). In other words, the PRV is a volume including the OAR 302, as well as an additional margin to compensate for uncertainties and/or variations relating to the precision or setup of a radiotherapy beam and/or relating to positional uncertainty of the OAR 302. As used herein, the terms OAR 302 and PRV may be used interchangeably. The OAR 302 may be located adjacent to a first side of the PTV 204, i.e. may be located in a first direction from the PTV 204. The OAR 302 may be a certain relative distance from the PTV 204. As used herein, a relative distance may also be referred to as a distance or a separation distance. This relative distance describes the distance between the OAR 302 and the target region/PTV 204 when one or more of the OAR 302 and the target region/PTV 204 may be moving, for example moving relative to each other. This relative distance may refer to the distance between the OAR 302 and the target region/PTV 204 at a particular timepoint. In this illustrative example, there may be no OAR 302 located at a similar or smaller distance from the PTV 204 in a second direction from the PTV 204 on a second side of the PTV 204 (i.e. to the left of FIG. 3a).

FIG. 3a also depicts a buffer region 304. The buffer region 304 comprises a shell disposed around the PTV 204. The buffer region 304 may be used in driving algorithms for controlling the radiotherapy device 100. For example, the buffer region 304 may be used in determining whether to adjust a radiotherapy treatment. The buffer region 304 may be determined based at least in part on the relative distance between the PTV 204 and the OAR 302. On the first side of the PTV 204, adjacent to the OAR 302, the buffer region may have a first width $w_1$. In some examples, and as shown in FIG. 3a, the first width $w_1$ may be equal to the relative distance between the PTV 204 and the OAR 302. In other examples, the first width $w_1$ may be equal to the relative distance plus or minus a particular absolute distance or a particular percentage of the absolute distance. These comprise options available for increasing or decreasing a sensitivity of a radiotherapy treatment to changes in position of a PTV 204 and/or OAR 302, and may be determined based on a balance between safety, efficiency, and/or a prognosis for a subject. Such determinations may be based on which particular organ the OAR 302 corresponds to (heart, brain, etc.) and/or a dose rate of the applied radiation.

The buffer region 304 may be anisotropic. The buffer region 304 may not be symmetrical along any particular plane, and may extend beyond the PTV 204 to different extents in different directions. In other words, the width of the buffer region 304 may not correspond to $w_1$ all the way around the PTV 204. As shown in FIG. 3a, the buffer region 304 has a second width $w_2$ in the second direction on the second side of the PTV 204. The second width $w_2$ may be larger than the first width $w_1$. The second width $w_2$ may be determined to be larger than the first width $w_1$ due to there being no OAR located on the second side of the PTV 204, or at least no OAR located as close to the second side of the PTV 204 as the OAR 302 is located to the first side of the PTV 204.

In some examples, the controller may first determine a constant buffer region 304 of first width $w_1$ based on the relative distance between the PTV 204 and the OAR 302 on the first side of the PTV 204, and may then increase the width of the buffer region 304 on other sides of the PTV 204 (for example to the second width $w_2$ in the second direction). The width of the buffer region 304 may be increased on these other sides until it reaches a different OAR, or until it comes within a predefined distance of an OAR, or until it reaches a predefined maximum extent. In some examples, the controller may first determine a constant buffer region 304 of second width $w_2$ based on there being no OAR on the second side of the PTV 204, and may then decrease the width of the buffer region 304 on other sides of the PTV 204 (for example to the first width $w_1$ in the first direction). The width of the buffer region 304 may be decreased on these other sides to prevent overlap with an OAR, or to prevent overlap with a location within a predefined distance of an OAR, or until it reaches a predefined minimum extent. The buffer region may be increased and/or decreased in width in different directions dynamically during a treatment, for example to accommodate movement of the subject, the PTV 204 and/or organs at risk as identified using the image data.

In some examples, the controller can determine, based on the image data, a shape of the PTV 204 and/or a shape of the OAR 302. The controller can determine the buffer region 304 around the PTV 204 based at least in part on the shape of the PTV 204 and/or the shape of the OAR 302. The shape of the PTV 204 and/or the shape of the organ at risk 302 may alternatively be predefined based on pre-treatment imaging or examination. The shape of the PTV 204 and/or the shape of the OAR 302 can be defined and considered in two dimensions or in three dimensions. These steps taking into account the shape of these regions can be performed in addition to or instead of the determination of the relative distance and the determination of the buffer region 304 based on this relative distance. The consideration of the shape(s) of the region(s) incorporates additional information regarding the PTV 204 and the OAR 302 relative to considering only a relative distance between these features. This can provide safer and more accurate control of a radiotherapy device through taking into account the spatial distribution of these features rather than just their separation distance. This has particular benefits when the shape of the PTV 204 is especially irregular (e.g. due to a tumour having an especially irregular shape) and/or when the shape of the OAR 302 is especially irregular.

FIG. 3b depicts corresponding features to those depicted in FIG. 3a and therefore repetition of the explanation of these features will be avoided. In FIG. 3b, relative to FIG. 3a, the PTV 204, the OAR 302 and the buffer region 304 have moved a distance d to the left. This may be due to the subject moving the distance d to the left. While in this example the movement of the subject has resulted in a corresponding movement of the PTV 204, the OAR 302 and the buffer region 304, in other examples one or more of these features may move by different amounts in different directions. This may be caused, for example, by internal parts of a subject moving relative to an external surface of the subject. Movement of the PTV 204, the OAR 302 and the subject as a whole may be directly or indirectly related to each other. The buffer region 304, being defined as a shell surrounding the PTV 204, may not move relative to the PTV 204 as such. However, the techniques described herein may lead to changes in the shape and size of the buffer region 304.

While FIG. 3b depicts an example in which the PTV 204, the OAR 302 and the buffer region 304 have moved a distance d to the left for ease of understanding, it will be understood that other movements are considered within the current disclosure. In some examples, one or more of the PTV 204, the OAR 302 and the buffer region 304 may undergo periodic motion, for example due to the subject's respiratory or cardiac cycle. In some examples, a location of one or more of the PTV 204, the OAR 302 and the buffer region 304 time-averaged over one of these cycles may be used in the determination of the relative distance and the buffer region.

In FIG. 3b, the treatment region 300 has not moved relative to FIG. 3a. In other words, the radiotherapy device 100 may be applying the same irradiation to a same location in FIG. 3b as in FIG. 3a. Since the PTV 204, the OAR 302 and the buffer region 304 have moved, and the treatment region 300 has not moved, the PTV 204, the OAR 302 and the buffer region 304 have moved relative to the treatment region 300. As can be seen from FIG. 3b, the treatment region 300 is located at least partially outside the buffer region 304. Specifically, a subset 306 (shown filled with diagonal lines) of the treatment region 300 is located outside the buffer region 304 in FIG. 3b.

According to the present disclosure, a controller may determine that the treatment region 300 is located at least partially outside the buffer region 304, i.e. determine the presence of the subset 306 of the treatment region 304 as shown in FIG. 3b. In particular, the image data can provide information on the location and/or movement of the subject and/or anatomical structures within the subject. For example, it can be identified from the image data when, by what distance and in what direction a PTV 204 has moved, e.g. based on a known anatomical structure of the PTV 204 and the surrounding tissue. Since the buffer region 304, being defined as a shell surrounding the PTV 204, does not move relative to the PTV 204 as such, a location and/or movement of the buffer region can be determined from the movement of the PTV 204 (i.e. can be determined from the image data). Therefore, since the treatment region 300 has not moved, and since the location of the buffer region 304 can be determined from the image data, whether the treatment region 300 is located at least partially outside the buffer region 304 can be determined. In other examples, the treatment region 300 may be moved, for example during a treatment. The controller may have information regarding this movement or may be communicatively coupled to components that transmit this information to the controller. The controller can therefore update the location of the treatment region 300 as appropriate in a time-dependent manner in applying the currently disclosed techniques.

In response to determining that the treatment region 300 is located at least partially outside the buffer region 304, the controller may generate a control signal for adjusting a radiotherapy treatment. The control signal may comprise one or more control signals transmitted to one or more components of the radiotherapy device. Where a control signal is described as being transmitted to multiple components, the whole of the control signal may be transmitted to each of the multiple components, or a separate part of the control signal may be sent to each component.

As described in more detail below, the controller can be configured to transmit the control signal to a treatment control apparatus. The treatment control apparatus may be communicatively coupled to the controller. The treatment control apparatus may be configured to receive the control signal and implement the control signal, for example by acting on computer-executable instructions comprised in the control signal. The treatment control apparatus may be configured to control or adjust a radiotherapy treatment based on the control signal. The treatment control apparatus may comprise one or more of a radiation source, beam-tracking or beam-shaping components such as a collimator 108 or multi-leaf collimator, a radiation source positioning system and a patient positioning surface.

The control signal may be configured to adjust an output of the radiation source. The control signal may be configured to gate and/or to reduce the dose rate of the radiation. In these examples, the control signal may be transmitted at least to the radiation source, and the control signal may cause the radiation source to gate and/or to reduce the dose rate of the radiation. As shown in FIG. 3b, the subset 306 of the treatment region 300 overlaps with the OAR 302. Therefore, this control signal may prevent damage to the OAR 302 by turning off the radiotherapy beam or reducing the dose rate of the radiotherapy beam.

Alternatively, or in addition, a control signal may be generated and transmitted to beam-tracking or beam-shaping components, such as to a collimator 108 (e.g. a multi-leaf collimator). This control signal may be configured to adjust a location of the treatment region 300, for example to reposition it within the buffer region 304. The control signal may be configured to cause the collimator 108 to adjust a shape of the radiotherapy beam. For example, the collimator 108 may be a multi-leaf collimator, and the control signal may be configured to adjust a location and/or an orientation of one or more leaves of the multi-leaf collimator. For example, these techniques can enable the radiotherapy beam to be tracked to avoid irradiating outside the buffer region 304. In some examples, a location and/or an orientation of one or more leaves of the multi-leaf collimator may be adjusted such that the radiotherapy beam is blocked in the subset 306 of the treatment region 300, causing the subset 306 of the treatment region not to be irradiated. Therefore, irradiation outside the buffer region 304, and inside the OAR 302, may be avoided.

Alternatively, or in addition, the control signal may be transmitted to a radiation source positioning system and may be configured to cause the radiation source positioning system to adjust a location and/or an orientation of the radiation source. The radiation source positioning system may be part of the gantry 116, or may couple the radiation source to the gantry 116. The radiation source positioning system may comprise a radiation source positioning system controller configured to receive the control signal and to implement the control signal by moving the radiation source positioning system and/or the radiation source.

Alternatively, or in addition, the control signal may be transmitted to a patient positioning surface (also referred to herein as a patient support surface) to adjust a location and/or an orientation of a patient positioning surface. This may enable a position of the target region relative to the radiation source to be adjusted. The patient positioning surface may be movable in three translational (x, y, z) and three rotational (roll, pitch, yaw) directions, i.e. its movement may have six degrees of freedom. The control signal may be configured to cause or adjust movement of the patient positioning surface in one, multiple or all of these directions. The patient positioning surface may comprise a patient positioning surface controller configured to receive the control signal and to implement the control signal by moving the patient positioning surface.

While FIG. 3b depicts an example in which the treatment region 300 has not moved relative to FIG. 3a for ease of understanding, it will be understood that in other examples the treatment region 300 may move between the first timepoint depicted in FIG. 3a and the second timepoint depicted in FIG. 3b. For example, the PTV 204 may vary in time during a treatment, and a radiotherapy beam may be tracked across a region of a subject to accommodate this. In these examples, the determination of a relative distance between an OAR 302 and a PTV 204 and the determination of a buffer region 304 based on this may be made using an updated location of the OAR 302 and/or an updated location of the PTV 204, which may be based on image data from one or more imaging systems. In some examples, the radiotherapy device may be configured such that the treatment region 300 moves within the PTV 204. In such examples, the controller may still be configured to generate a control signal to adjust the radiotherapy treatment if the treatment region 300 is located at least partially outside the buffer region 304 at a particular timepoint.

The controller may be configured to receive image data from the one or more imaging systems, determine the relative distance, determine the buffer region, generate the control signal and/or transmit the control signal during a radiotherapy treatment. One or more of these steps may be performed multiple times or continuously during a radiotherapy treatment. The controller may be configured to receive image data from the one or more imaging systems, determine the relative distance, determine the buffer region, generate the control signal and/or transmit the control signal in real-time during a radiotherapy treatment. The controller may be configured to receive image data from the one or more imaging systems, determine the relative distance, determine the buffer region, generate the control signal and/or transmit the control signal dynamically during a radiotherapy treatment. Performing one or more of these steps during a radiotherapy treatment, in this dynamic/real-time manner, may be based on data from an MR imaging system. By enabling such dynamic variation of the buffer region during a radiotherapy treatment, more appropriate/more accurate safety margins may be implemented so as to reduce the interruption of and increase the efficiency of the radiotherapy treatment.

In some examples, it may be determined whether the subject or a part of the subject has moved, and one or more of receiving image data from the one or more imaging systems, determining the relative distance, determining the buffer region, generating the control signal and/or transmitting the control signal may be performed in response to determining that the subject or a part of the subject has moved. In some examples, if it is determined at a subsequent time point that the subject or a part of the subject has moved back to a previous location associated with a previous time point, the relative distance associated with the previous time point may be used as the relative distance for the subsequent time point and/or the buffer region associated with the previous time point may be used as the buffer region for the subsequent time point. Determination of whether the subject or a part of the subject has moved may be based on the image data. Alternatively, or in addition, determination of whether the subject or a part of the subject has moved may be based on one or more other sensors such as a chest strap or cameras in the room in which the radiotherapy treatment is being performed.

In some examples, if it is determined that the subject or a part of the subject has not moved relative to a previous time point, one or more of receiving image data from the one or more imaging systems, determining the relative distance, determining the buffer region, generating the control signal and/or transmitting the control signal may not be performed, at least until a subsequent time point. In other words, a buffer region from the previous time point may be retained/kept in use in response to determining that the subject or a part of the subject has not moved relative to the previous time point.

In some examples, determining a buffer region may comprise adjusting a previous buffer region, for example a part of the previous buffer region. For example, a first side of a buffer region may be adjusted based on the relative distance to an organ at risk on the first side having changed, for example having changed dynamically during treatment. The second side of the buffer region may remain unchanged, i.e. the part of the previous buffer region corresponding to the second side may be used for the second side of the adjusted buffer region. This may be based on the anatomy in the vicinity of the second side remaining unchanged relative to the time point at which the previous buffer region was determined. The anatomy remaining unchanged may indicate that an organ at risk on the second side is at the same distance from the target region on the second side, or at the same distance within a predetermined threshold, or that there is no organ at risk on the second side.

These steps enable improved use of previously determined distances and regions and enable implementation of processing steps only when needed or justified based on the progress of the radiotherapy treatment. Therefore, these steps can increase the efficiency of the use of the available computational resources and can increase the speed with which a control signal is generated for adjusting the radiotherapy treatment.

In some examples, the target region may move according to a first vector while the organ at risk remains stationary or moves according to a second vector. In other examples, the organ at risk may move according to a first vector while the target region remains stationary or moves according to a second vector. For example, this may be due to the effects of gravity, the anatomy of the subject, the nature of the movement and/or one or more physiological cycles of the subject, such as respiration or cardiac motion. The target region and/or the organ at risk and/or the buffer region may move with the movement of the subject, while the treatment region may be controlled to move with respect to the frame of the room in which the radiotherapy treatment is being performed.

According to the present disclosure, the controller may determine a relative distance between the PTV 204 and the OAR 302 from image data, and the controller may determine whether the treatment region 304 is located at least partially outside the buffer region 300 based on image data. The image data may be generated by one or more imaging systems. In some examples, the relative distance may be determined from image data taken at a first timepoint, for example at a timepoint depicted in FIG. 3*a*, and the treatment region 300 may be determined to be located at least partially outside the buffer region 304 based on image data taken at a second (later) timepoint, for example at a timepoint depicted in FIG. 3*b*. The first width $w_1$ and the second width $w_2$ have not been depicted in FIG. 3*b* for ease of understanding. However, it will be understood that, as the PTV 204, the OAR 302 and the buffer region 304 have each moved a distance d to the left in FIG. 3*b*, a corresponding relative distance between the PTV 204 and the OAR 302, a corresponding first width $w_1$ and a corresponding second width $w_2$ are each applicable to FIG. 3*b* as they are to FIG. 3*a*. Therefore, the relative distance between the PTV 204 and the OAR 302 may alternatively be determined from the same image data based on which the treatment region 300 is determined to be located at least partially outside the buffer region 304, i.e. at the second timepoint depicted in FIG. 3*b*. In other words, since the relative distance between the PTV 204 and the OAR 302 in FIG. 3*b* is the same as the relative distance in FIG. 3*a*, the same buffer region (with the same first and second widths $w_1$ and $w_2$) can be derived from this relative distance.

Image data for the PTV 204 and/or the OAR 302 may be time-dependent, and may be generated continuously, at intervals, at predefined timepoints and/or at the prompting of a clinician. This generation may occur during a radiotherapy treatment. In some examples, the first time point depicted in FIG. 3*a* may be during a radiotherapy treatment. In other examples, the first timepoint depicted in FIG. 3*a* may be before the start of a radiotherapy treatment, e.g. with the subject in a treatment position. In some examples, the steps of determining the relative distance and determining the buffer region may be performed based on image data generated by a first imaging system, e.g. a dedicated CT (computed tomography) scanner, a CBCT (cone beam computed tomography) scanner, a portal imaging system such as an electronic portal imaging device (EPID), a PET (positron emission tomography) scanner or an ultrasound imaging system. In some examples, the step of generating a control signal in response to determining that the treatment region 300 is located at least partially outside the buffer region 304 may be performed based on image data generated by a second imaging system, e.g. an MR imaging system. This image data may be generated during a radiotherapy treatment. The pre-treatment determination of the relative distance and the buffer region may be used to determine an initial treatment plan. In some examples, the relative distance and the buffer region can be redetermined during radiotherapy treatment to dynamically update the treatment plan, for example based on image data from the MR imaging system. Where image data generated by one or more imaging systems is referred to herein, all of the image data can be generated by a first imaging system, all of the image data can be generated by a second (or third, fourth, etc.) imaging system, or different parts of the image data can be generated by different imaging systems of the one or more imaging systems.

The controller may use the image data to continuously, at intervals, at predefined timepoints and/or at the prompting of a clinician determine or update the relative distance and/or the buffer region 304. The controller may use the image data to continuously, at intervals, at predefined timepoints and/or at the prompting of a clinician determine whether the treatment region 300 is located at least partially outside the buffer region, generate a control signal, and/or transmit the control signal to one or more components of the radiotherapy device. Therefore, these quantities and determinations may be dynamically recalculated during a radiotherapy treatment, which can increase the accuracy and safety of the radiotherapy treatment. In this manner, movement of the different regions and physical features of the subject during a radiotherapy treatment can be taken into account.

One or more of the PTV 204, treatment region 300, OAR 302, buffer region 304 and subset 306 of the treatment region 300 may be a two-dimensional region (i.e. an area) or a three-dimensional region (i.e. a volume). In other words, these features may be considered, stored, calculated and/or determined by the controller in two dimensions or three dimensions, according to the particular application, requirements, available sensors, available data and available processing power.

It will be understood that gating the treatment beam enables selectively applying radiation in some time periods and not in others. The radiation source may comprise a particle source, for example an electron source 106 and a radiofrequency (RF) field source 102 (as shown in FIG. 1). The electron source may provide a source of electrons which generate a radiation dose to be delivered to the subject, for example by impacting a target. The RF field source may electromagnetically accelerate the electrons to a desired velocity suitable for providing the radiation dose. The radiation source may be gated by selectively controlling the electron source to be on (active) or off (inactive). Alternatively, or in addition, the radiation source 100 may be gated by selectively controlling the RF field source to be on (active) or off (inactive). In this manner, application of a radiation dose by the radiation source can be controlled according to desired parameters, for example based on a control signal according to the present disclosure.

The radiation source may comprise a radiation source controller suitable for controlling the radiation source, for example by gating the radiation source, stopping gating of the radiation source and/or adjusting a dose rate of the radiation source. The controller may transmit the control signal to the radiation source controller. The control signal may comprise instructions for effecting such gating or stopping such gating or adjusting the dose rate immediately, at a defined later time, after a defined interval, or some combination of these. The control signal may therefore comprise instructions for time-varying or time-dependent gating of the beam by the radiation source and/or adjustment of the dose rate by the radiation source.

Figure 4:
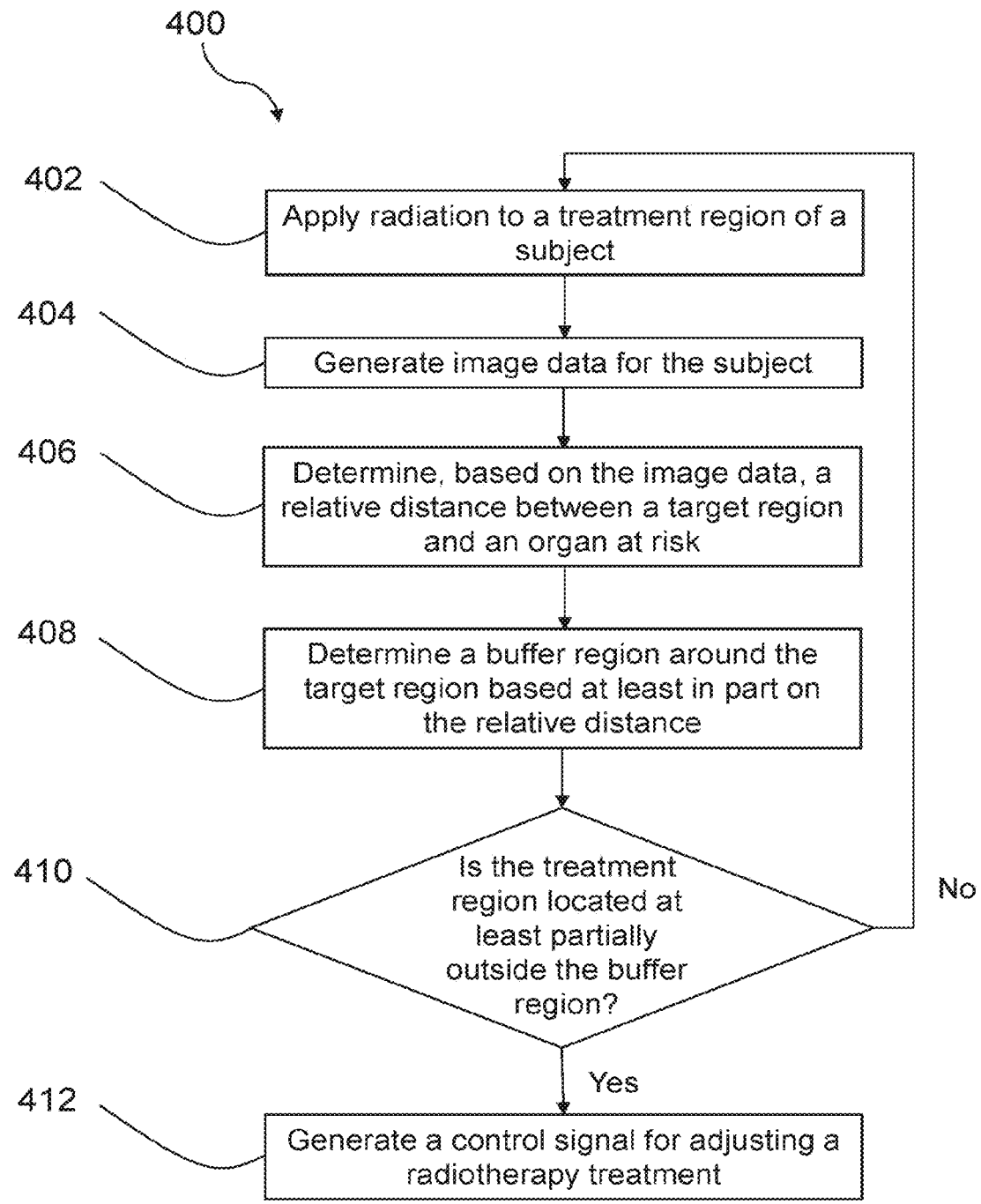
FIG. 4 depicts a method of controlling a radiotherapy device according to the present disclosure.

FIG. 4 depicts a method 400 of controlling a radiotherapy device according to the present disclosure. The method may be performed using the radiotherapy device 100 as presently disclosed. The method may be a computer-implemented method.

In a step 402, radiation may be applied to a treatment region 300 of a subject. The radiation may be applied by the radiation source. The radiation may be applied according to a treatment plan.

In a step 404, image data may be generated for the subject. The image data may be generated by one or more imaging systems, which may comprise a magnetic resonance (MR) imaging system. The image data may be two-dimensional or three-dimensional. The image data may be of a whole of the subject or may be of a subset of the subject including the treatment region 300 and/or the target region/PTV 204. The image data may be generated repeatedly or continuously during a radiotherapy treatment, i.e. while radiation is applied to the subject. Alternatively, or in addition, the image data may be generated at a series of predetermined timepoints and/or at the prompting of a clinician. In some examples, at least a part of the image data may be generated before the start of a treatment.

In a step 406, a relative distance between the target region/PTV 204 and the organ at risk 302 may be determined based on the image data. The determination may be made by a controller communicatively coupled to the radiation source and the one or more imaging systems. The one or more imaging systems may transmit the image data to the controller. This transmission may be made repeatedly or continuously during a radiotherapy treatment, i.e. while radiation is applied to the subject. Alternatively, or in addition, the transmission may be made at a series of predetermined timepoints and/or at the prompting of a clinician. The relative distance may be a vector between the target region 204 and the organ at risk 302. The vector may be defined in two dimensions or three dimensions. The relative distance may be defined as the smallest distance between a surface of the target region 204 and a surface of the organ at risk 302. The surface of the target region 204 may be an isodose surface of the target region. Alternatively, the relative distance may be determined as the distance between a centre of mass of the target region 204 and a centre of mass of the organ at risk 302.

In a step 408, a buffer region 304 may be determined around the target region 204 based at least in part on the relative distance. The determination may be made by the controller. The buffer region may be anisotropic. The buffer region may extend beyond the target region by different distances in different directions. For a first direction from the target region 204 to an organ at risk 302, and a second direction different from the first direction, the buffer region may extend a smaller distance (i.e. be thinner) in the first direction than in the second direction.

In a step 410, it may be determined whether the treatment region 300 is located at least partially outside the buffer region 304. In other words, it may be determined whether a non-zero subset 306 of the treatment region 300 is located outside the buffer region 304. The determination may be made by the controller. The determination may be based at least in part on image data for the subject. The image data may be the same image data referred to in step 404 and step 406 above. Alternatively, the image data may be image data taken at a later timepoint. The one or more imaging systems may comprise a magnetic resonance imaging (MRI) system. The image data may be two-dimensional or three-dimensional. The image data may be of a whole of the subject or may be of a subset of the subject including the treatment region 300 and/or the target region 204. The image data may be generated repeatedly or continuously during a radiotherapy treatment, i.e. while radiation is applied to the subject. Alternatively, or in addition, the image data may be generated at a series of predetermined timepoints and/or at the prompting of a clinician. In some implementations, the determination may comprise determining whether the treatment region 300 extends beyond the buffer region 304 by at least a threshold amount. The threshold amount may be an absolute volume or a percentage of the treatment region 300 or the target region 204.

In response to a determination that the treatment region 300 is not at least partly outside the buffer region 304, the method may return to step 402. Steps 402-410 may be performed continuously or at intervals. In response to a determination that the treatment region 300 is at least partly outside the buffer region 304, the method may continue to step 412.

In the step 412, a control signal may be generated for adjusting a radiotherapy treatment. The control signal may be generated by the controller. The control signal may be configured to adjust an output of the radiation source. The control signal may be configured to gate the radiation source. Alternatively, or in addition, the control signal may be configured to adjust (e.g. reduce) the dose rate of the radiation applied by the radiation source. The dose rate may be reduced based on a size of the subset 306 of the treatment region 300 that is located outside the buffer region 304. In particular, the control signal may be configured to reduce the dose rate by a larger amount if a larger subset 306 of the treatment region 300 is located outside the buffer region 304 and by a smaller amount if a smaller subset 306 of the treatment region 300 is located outside the buffer region 304. Alternatively, or in addition, the control signal may be configured to cause a radiation source positioning system to adjust a location and/or an orientation of the radiation source. Alternatively, or in addition, the control signal may be configured to cause a collimator 108 to adjust a shape of the radiotherapy beam. For example, the collimator 108 may be a multi-leaf collimator, and the control signal may be configured to adjust a location and/or an orientation of one or more leaves of the multi-leaf collimator. Alternatively, or in addition, the control signal may be configured to adjust a location and/or an orientation of a patient positioning surface. This may enable a position of the target region relative to the radiation source to be adjusted.

In some examples, the controller may only generate the control signal for adjusting the output of the radiation source if the current dose rate is above a predefined threshold and/or if the treatment region 300 is located at least partially outside the buffer region 304 for at least a predefined time period. This accommodates the fact that an organ at risk 302 may be able to withstand being irradiated at a small or moderate dose rate for a small or moderate amount of time. This avoids unnecessarily halting a radiotherapy treatment and thereby increases an efficiency of radiotherapy treatment. The controller may determine the dose applied to the organ at risk or a part thereof based on the image data and based on a multiplication of the dose rate and the amount of time the treatment region 300 is located at least partially outside the buffer region 304. In other words, the controller may be configured to generate and/or transmit the control signal further based on determining that a current dose rate is above a predefined threshold and/or further based on determining that the treatment region 300 has been located at least partially outside the buffer region 304 for at least a predefined time period. In response to determining that the treatment region 300 is located at least partially outside the buffer region 304, the controller may introduce a delay before generating or transmitting the control signal and may only generate or transmit the control signal if the dose rate is above the predefined threshold and/or if the treatment region 300 has been located at least partially outside the buffer region 304 for at least a predefined time period.

The control signal may be transmitted to one or more components of the radiotherapy device, such as the radiation source, the radiation source positioning system, the collimator 108 or multi-leaf collimator and/or the patient positioning surface. The control signal may be transmitted by the controller. The control signal may cause the radiation source to gate the radiation, for example by turning off a source of electrons or by turning off an RF field for accelerating the electrons. Alternatively, or in addition, the control signal may control the radiation source to reduce the dose rate applied by the radiation source, for example by reducing the source of electrons or by reducing the RF field. Alternatively, or in addition, the control signal may cause the radiation source positioning system to adjust a location and/or orientation of the radiation source. Alternatively, or in addition, the control signal may cause the collimator to adjust a shape of a radiotherapy beam emitted by the radiation source (i.e. to adjust the shape of the radiotherapy beam subsequent to its emission by the radiation source). Alternatively, or in addition, the control signal may cause adjustment of a location and/or an orientation of a patient positioning surface.

The one or more imaging systems may continue to generate image data following transmission and/or implementation of the control signal. The controller may use this image data to determine whether the treatment region 300 continues to be located at least partly outside the buffer region 304. If the treatment region 300 is no longer at least partly located outside the buffer region 304 at a later timepoint, the controller may generate a further control signal, and may transmit this further control signal to the radiation source. The further control signal can be configured to cause the radiation source to apply radiation, to increase the dose rate of the radiation applied, to cause a radiation source positioning system to adjust a location and/or orientation of the radiation source, to cause the collimator 108 to adjust the shape of the radiotherapy beam, and/or to adjust a location and/or orientation of a patient positioning surface.

Figure 5:
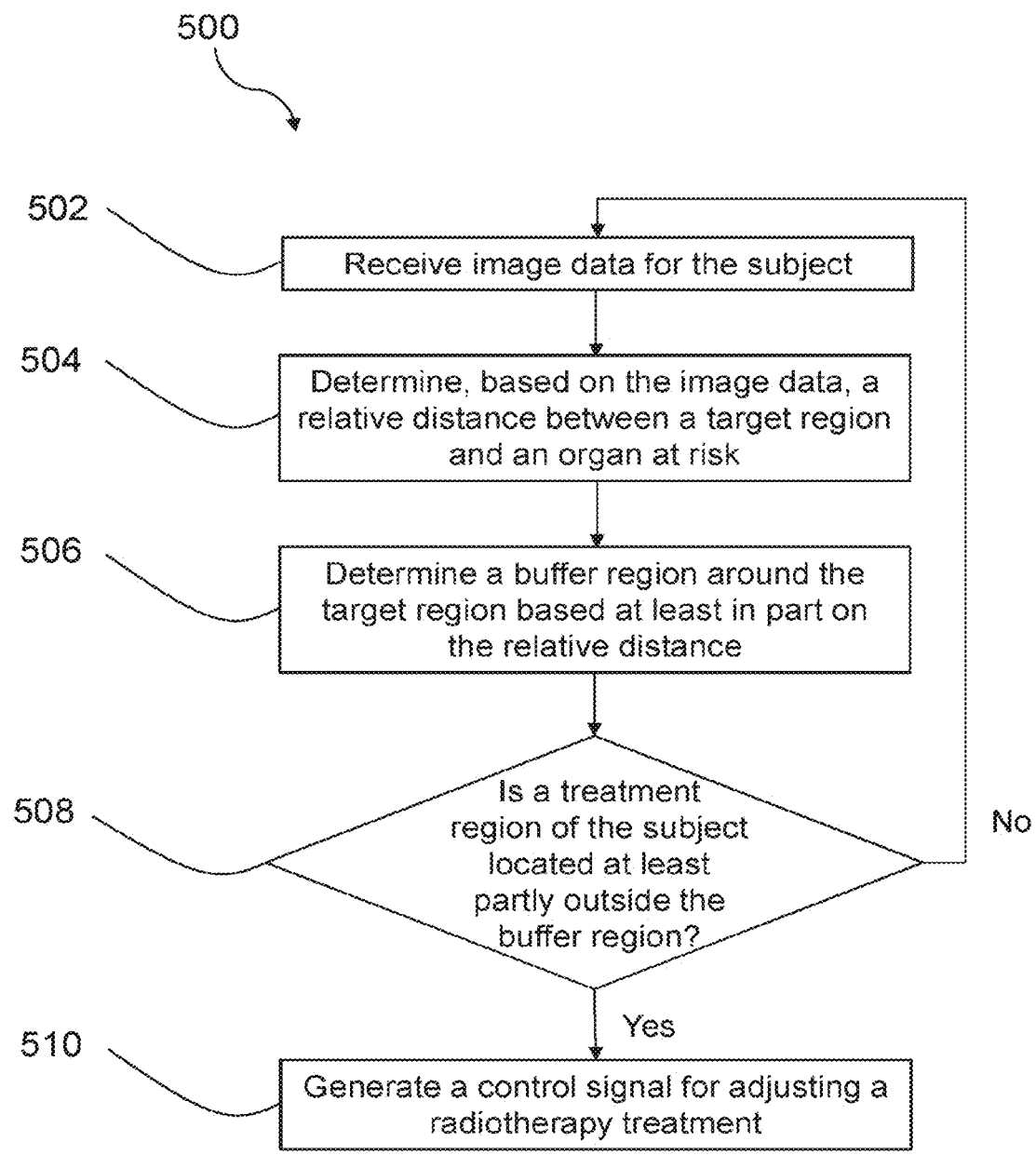
FIG. 5 depicts a method of generating a control signal for controlling a radiotherapy device according to the present disclosure.

FIG. 5 depicts a method 500 of generating a control signal for a radiotherapy device according to the present disclosure. The method may be performed using a controller of the radiotherapy device 100 as presently disclosed. The method may be a computer-implemented method. Where steps of the method 500 correspond to or are similar to respective steps of the method 400, it will be understood that corresponding features and/or explanations may apply.

In a step 502, image data may be received for the subject. The image data may be generated by and received from one or more imaging systems. The one or more imaging systems may comprise a magnetic resonance (MR) imaging system. The image data may be two-dimensional or three-dimensional. The image data may be of a whole of the subject or may be of a subset of the subject including the treatment region 300 and/or a target region 204. The image data may be generated repeatedly or continuously during a radiotherapy treatment, i.e. while radiation is applied to the subject. Alternatively, or in addition, the image data may be generated at a series of predetermined timepoints and/or at the prompting of a clinician. In some examples, at least a part of the image data may be generated before the start of a treatment.

In a step 504, a relative distance between a target region 204 and an organ at risk 302 may be determined based on the image data. The relative distance may be a vector between the target region 204 and the organ at risk 302. The vector may be defined in two dimensions or three dimensions. The relative distance may be defined as the smallest distance between a surface of the target region and a surface of the organ at risk 302. The surface of the target region 204 may be an isodose surface of the target region 204. Alternatively, the relative distance may be determined as the distance between a centre of mass of the target region 204 and a centre of mass of the organ at risk 302.

In a step 506, a buffer region 304 may be determined around the target region 204 based at least in part on the relative distance. The determination may be made by the controller. The buffer region 304 may be anisotropic. The buffer region 304 may extend beyond the target region 204 by different distances in different directions. For a first direction from the target region 204 to an organ at risk 302, and a second direction different from the first direction, the buffer region 304 may extend a smaller distance (i.e. be thinner) in the first direction than in the second direction.

In a step 508, it may be determined whether a treatment region 300 of the subject is located at least partly outside the buffer region 304. In other words, it may be determined whether a non-zero subset 306 of the treatment region 300 is located at least partially outside the buffer region 304. The determination may be based at least in part on image data for the subject. The image data may be the same image data referred to in step 502 and step 504 above. Alternatively, the image data may be image data taken at a later timepoint. The one or more imaging systems may comprise a magnetic resonance (MR) imaging system. The image data may be two-dimensional or three-dimensional. The image data may be of a whole of the subject or may be of a subset of the subject including the treatment region 300 and/or the target region 204. The image data may be generated repeatedly or continuously during a radiotherapy treatment, i.e. while radiation is applied to the subject. Alternatively, or in addition, the image data may be generated at a series of predetermined timepoints and/or at the prompting of a clinician. In some implementations, it may be determined whether the treatment region 300 extends beyond the buffer region 304 by at least a threshold amount. The threshold amount may be an absolute volume or a percentage of the treatment region 300 or the target region 204.

In response to a determination that the treatment region 300 is not at least partly outside the buffer region 304, the method may return to step 502. Steps 502-508 may be performed continuously or at intervals. In response to a determination that the treatment region 300 is at least partly outside the buffer region 304, the method may continue to step 510.

In the step 510, a control signal may be generated for adjusting a radiotherapy treatment. The control signal may be configured to adjust an output of the radiation source. The control signal may be configured to gate the radiation source. Alternatively, or in addition, the control signal may be configured to adjust (e.g. reduce) the dose rate of the radiation applied by the radiation source.

Alternatively, or in addition, the control signal may be configured to cause a radiation source positioning system to adjust a location and/or orientation of the radiation source. Alternatively, or in addition, the control signal may be configured to cause a collimator 108 to adjust a shape of a radiotherapy beam emitted by the radiation source (i.e. to adjust the shape of the radiotherapy beam subsequent to its emission by the radiation source). Alternatively, or in addition, the control signal may be configured to adjust a location and/or an orientation of a patient positioning surface.

The controller may continue to receive image data following transmission of the control signal. The controller may use this image data to determine whether a treatment region 300 continues to be located at least partly outside the buffer region. If the treatment region 300 is no longer at least partly located outside the buffer region 304 at a later timepoint, the controller may generate a further control signal, and may transmit this further control signal to the radiation source. The further control signal can be configured to cause the radiation source to apply radiation, to increase the dose rate of the radiation applied, to cause a radiation source positioning system to adjust a location and/or orientation of the radiation source, to cause the collimator 108 to adjust the shape of the radiotherapy beam, and/or to adjust a location and/or an orientation of a patient positioning surface.

The apparatus disclosed herein may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

There is provided herein a computer-implemented method comprising: receiving image data for a subject from one or more imaging systems; determining, based on the image data, a relative distance between a target region and an organ at risk; determining a buffer region around the target region based at least in part on the relative distance; and generating a control signal for adjusting a radiotherapy treatment in response to a treatment region of the subject being located at least partially outside the buffer region.

The computer-implemented method may comprise transmitting the control signal to a radiation source, wherein the control signal is configured to adjust an output of the radiation source. The control signal may be configured to cause the radiation source to gate the application of radiation. The control signal may be configured to cause the radiation source to reduce a dose rate of the radiation. The control signal may be configured to cause the radiation source to reduce the dose rate of the radiation based on a size of a subset of the treatment region that is located outside the buffer region.

The computer-implemented method may comprise transmitting the control signal to a radiation source positioning system, wherein the control signal is configured to cause the radiation source positioning system to adjust a location and/or an orientation of the radiation source.

The computer-implemented method may comprise transmitting the control signal to a collimator, wherein the control signal is configured to cause the collimator to adjust a shape of a radiotherapy beam emitted by the radiation source. The collimator may be a multi-leaf collimator, wherein the control signal being configured to cause the collimator to adjust the shape of the radiotherapy beam comprises the control signal being configured to adjust a location and/or orientation of one or more leaves of the multi-leaf collimator.

The computer-implemented method may comprise transmitting the control signal to a patient positioning surface, wherein the control signal is configured to adjust a location and/or an orientation of the patient positioning surface.

The buffer region may be anisotropic. The buffer region may extend beyond the target region by different distances in different directions. A first width of the buffer region in a first direction in which the organ at risk is located may be smaller than a second width of the buffer region in a second direction in which no organ at risk is located.

The computer-implemented method may comprise determining, based on the image data, a shape of the target region and/or a shape of the organ at risk; and determining the buffer region around the target region based at least in part on the shape of the target region and/or the shape of the organ at risk.

The computer-implemented method may comprise generating and/or transmitting the control signal further based on determining that a current dose rate is above a predefined threshold and/or further based on determining that the treatment region has been located at least partially outside the buffer region for at least a predefined time period.

The image data may be three-dimensional image data, wherein the computer-implemented method comprises determining the relative distance in three dimensions, determining the buffer region in three dimensions, and determining whether the treatment region is located at least partially outside the buffer region in three dimensions. The one or more imaging systems may comprise a magnetic resonance imaging system.

The computer-implemented method may comprise receiving image data from the one or more imaging systems, determining the relative distance, determining the buffer region, generating the control signal and/or transmitting the control signal multiple times or continuously during a radiotherapy treatment.

The computer-implemented method may comprise determining, based on the image data, respective relative distances between the target region and each of multiple organs at risk; and determining the buffer region around the target region based at least in part on the relative distances.

Figure 6:
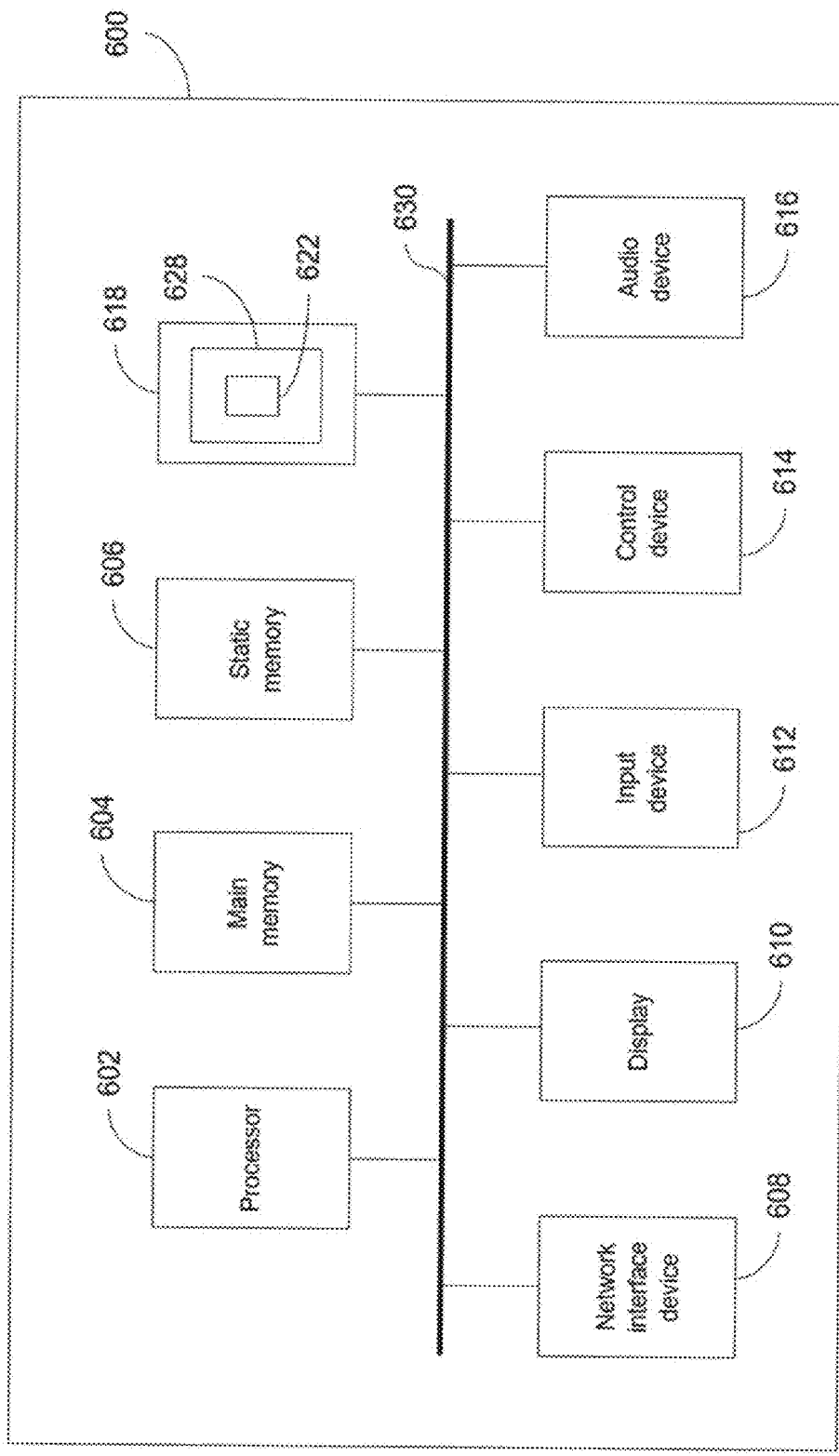
FIG. 6 depicts a block diagram of a computing device configured to perform one or more of the methods described herein.

FIG. 6 illustrates a block diagram of one implementation of a computing device 600 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 600 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a secondary memory (e.g., a data storage device 618), which communicate with each other via a bus 630.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 622) for performing the operations and steps discussed herein.

The computing device 600 may further include a network interface device 608. The computing device 600 also may include a video display unit 610 (e.g., a liquid crystal display (LCD) or a cathode ray tube (CRT)), an alphanumeric input device 612 (e.g., a keyboard or touchscreen), a cursor control device 614 (e.g., a mouse or touchscreen), and an audio device 616 (e.g., a speaker).

The data storage device 618 may include one or more machine-readable storage media (or more specifically one or more non-transitory computer-readable storage media) 628 on which is stored one or more sets of instructions 622 embodying any one or more of the methodologies or functions described herein. The instructions 622 may also reside, completely or at least partially, within the main memory 604 and/or within the processing device 602 during execution thereof by the computer system 600, the main memory 604 and the processing device 602 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A radiotherapy device comprising:
a radiation source configured to apply radiation to a treatment region coinciding with a subject according to a treatment plan;
one or more imaging systems configured to generate image data of the subject; and
a controller communicatively coupled to the radiation source and to the one or more imaging systems, the controller being configured to:
determine, based on the image data, a relative distance between a target region of the subject and an organ at risk of the subject, wherein the treatment plan comprises a prescribed dose for the target region;
determine a buffer region around the target region based at least in part on the relative distance; and
generate a control signal for adjusting a radiotherapy treatment in response to determining, based on the image data, that the treatment region is located at least partially outside the buffer region.

2. The radiotherapy device according to claim 1, wherein the controller is configured to;
transmit the control signal to the radiation source, wherein the control signal is configured to adjust an output of the radiation source.

3. The radiotherapy device according to claim 2, wherein the control signal is configured to at least one of:
cause the radiation source to gate application of radiation; or
cause the radiation source to reduce a dose rate of the radiation.

4. The radiotherapy device according to claim 3, wherein the control signal is configured to cause the radiation source to reduce the dose rate of the radiation based on a size of a subset of the treatment region that is located outside the buffer region.

5. The radiotherapy device according to claim 1, wherein the controller is configured to at least one of:
transmit the control signal to a radiation source positioning system, wherein the control signal is configured to cause the radiation source positioning system to adjust at least one of a location or an orientation of the radiation source;
transmit the control signal to a collimator, wherein the control signal is configured to cause the collimator to adjust a shape of a radiotherapy beam emitted by the radiation source; or
transmit the control signal to a patient positioning surface, wherein the control signal is configured to adjust a location and/or an orientation of the patient positioning surface.

6. The radiotherapy device according to claim 1, wherein the controller is configured to transmit the control signal to is a multi-leaf collimator, and wherein the control signal is configured to adjust at least one of a location or orientation of one or more leaves of the multi-leaf collimator.

7. The radiotherapy device according to claim 1, wherein the controller is configured to:
transmit the control signal to a patient positioning surface, wherein the control signal is configured to adjust at least one of a location or an orientation of the patient positioning surface.

8. The radiotherapy device according to claim 1, wherein the buffer region is anisotropic.

9. The radiotherapy device according to claim 1, wherein the buffer region extends beyond the target region by different distances in different directions.

10. The radiotherapy device according to claim 1, wherein a first width of the buffer region in a first direction in which the organ at risk is located is smaller than a second width of the buffer region in a second direction in which no organ at risk is located.

11. The radiotherapy device according to claim 1, wherein the controller is configured to:
determine, based on the image data at least one of, a shape of the target region or a shape of the organ at risk; and
determine the buffer region around the target region based at least in part on at least one of the shape of the target region or the shape of the organ at risk.

12. The radiotherapy device according to claim 1, wherein the controller is configured to at least one of generate or transmit the control signal based on at least one of determining that a current dose rate is above a predefined threshold or determining that the treatment region has been located at least partially outside the buffer region for at least a predefined time period.

13. The radiotherapy device according to claim 1, wherein the image data includes three-dimensional image data, and wherein the controller is configured to determine the relative distance in three dimensions, determine the buffer region in three dimensions, and determine whether the treatment region is located at least partially outside the buffer region in three dimensions.

14. The radiotherapy device according to claim 1, wherein the one or more imaging systems comprise a magnetic resonance imaging system.

15. The radiotherapy device according to claim 1, wherein the controller is configured to at least one of receive image data from the one or more imaging systems, determine the relative distance, determine the buffer region, generate the control signal, or transmit the control signal multiple times or continuously during a radiotherapy treatment.

16. The radiotherapy device according to claim 1, wherein the controller is configured to:
determine, based on the image data, respective relative distances between the target region and each of multiple organs at risk; and
determine the buffer region around the target region based at least in part on the relative distances.

17. A computer-implemented method comprising:
receiving image data of a subject from one or more imaging systems;
determining, based on the image data, a relative distance between a target region of the subject and an organ at risk of the subject, wherein a treatment plan comprises a prescribed dose for the target region;
determining a buffer region around the target region based at least in part on the relative distance; and
generating a control signal for adjusting a radiotherapy treatment in response to a treatment region coinciding with the subject being located at least partially outside the buffer region.

18. The computer-implemented method according to claim 17, wherein the computer-implemented method comprises:
transmitting the control signal to one or more of a radiation source, a radiation source positioning system, a collimator, a multi-leaf collimator, or a patient positioning surface.

19. The computer-implemented method according to claim 17, wherein at least one of:
the buffer region is anisotropic;
the buffer region extends beyond the target region by different distances in different directions; or a first width of the buffer region in a first direction in which the organ at risk is located is smaller than a second width of the buffer region in a second direction in which no organ at risk is located.

20. The computer-implemented method according to claim 17, wherein the computer-implemented method comprises:
   determining, based on the image data, at least one of a shape of the target region or a shape of the organ at risk; and
   determining the buffer region around the target region based at least in part on at least one of the shape of the target region or the shape of the organ at risk.

21. A computer-implemented method according to claim 17, wherein the computer-implemented method comprises:
   at least one of generating or transmitting the control signal based on at least one of:
   determining that a current dose rate is above a predefined threshold; or
   determining that the treatment region has been located at least partially outside the buffer region for at least a predefined time period.

22. The computer-implemented method according to claim 17, wherein at least one of:
   the image data is three-dimensional image data, and the computer-implemented method comprises determining the relative distance in three dimensions, determining the buffer region in three dimensions, and determining whether the treatment region is located at least partially outside the buffer region in three dimensions;
   the computer-implemented method comprises receiving image data from the one or more imaging systems, determining the relative distance, determining the buffer region, and at least one of generating the control signal or transmitting the control signal multiple times or continuously during a radiotherapy treatment; or
   the computer-implemented method comprises determining, based on the image data, respective relative distances between the target region and each of multiple organs at risk and determining the buffer region around the target region based at least in part on the relative distances.

23. A non-transitory computer-readable medium comprising computer executable instructions which, when executed by a processor, cause the processor to perform operations, the operations comprising:
   receiving image data of a subject from one or more imaging systems;
   determining, based on the image data, a relative distance between a target region of the subject and an organ at risk of the subject, wherein a treatment plan comprises a prescribed dose for the target region;
   determining a buffer region around the target region based at least in part on the relative distance; and
   generating a control signal for adjusting a radiotherapy treatment in response to a treatment region coinciding with the subject being located at least partially outside the buffer region.

* * * * *